United States Patent [19]
Taketomo et al.

[11] Patent Number: 6,007,813
[45] Date of Patent: Dec. 28, 1999

[54] METHOD AND COMPOSITION FOR TREATING ULCERS AND SECRETION OF GASTRIC ACID

[75] Inventors: Naoki Taketomo; Akinobu Tsunoo, both of Tokyo; Hiroyuki Itoh, Kanagawa, all of Japan

[73] Assignee: Meiji Milk Products Company Limited, Tokyo, Japan

[21] Appl. No.: 09/181,748

[22] Filed: Oct. 29, 1998

Related U.S. Application Data

[60] Division of application No. 08/777,110, Dec. 30, 1996, which is a continuation-in-part of application No. PCT/JP95/01298, Jun. 29, 1995.

[30] Foreign Application Priority Data

Jun. 30, 1994 [JP] Japan .................................. 6-170481

[51] Int. Cl.⁶ .............................. A61K 35/00; C12P 1/02; C12P 19/00
[52] U.S. Cl. ........................... 424/115; 424/123; 435/41; 435/72; 435/101; 435/171; 514/23; 514/54; 514/826; 514/929
[58] Field of Search .................................. 424/115, 123; 435/41, 72, 101, 171; 514/23, 54, 925, 926, 927

[56] References Cited

U.S. PATENT DOCUMENTS

| | | |
|---|---|---|
| 4,225,673 | 9/1980 | Sugiura et al. . |
| 4,820,689 | 4/1989 | Ikuzawa et al. . |
| 5,281,583 | 1/1994 | Soma et al. . |

FOREIGN PATENT DOCUMENTS

| | | |
|---|---|---|
| 54-080486 | 6/1979 | Japan . |
| 63-166815 | 7/1988 | Japan . |
| 1-206991 | 11/1989 | Japan . |

OTHER PUBLICATIONS

Kiho et al., Biol. Pharm. Bull., vol. 16 (12), pp. 1291–1293, (1993).

Yoshida et al., Japan J. Exp. Med., vol. 59 (4), pp. 157–161, (1989).

Hamada, J. Kanazawa Med. Univ., vol. 16, pp. 46–54, (1991).

Kurokawa, M. et al., "Parasympathetic depression of vas deferens contraction in the guinea–pig involves adenosine receptors." Journal Of Physiology, vol. 407, pp. 135–153, (1988).

Tsunoo, A. et al., "Neurally evoked potentation of tonic contrations in the guinea–pig vas deferens involves adenosine receptors," *Journal Of Physiology,* vol. 443, pp. 163–181, (1991).

Tsunoo, A. et al., "Pharmacological Effects Of The Mycelial Extract Of Cultured Cordyceps Sinensis On Airways And Aortae Of The Rat," Science and Cultivation of Edible Fungi, Elliot, T. ed., Proceedings of the 14th International Congress on the Science and Cultivation of Edible Fungi, (1995).

Manabe, N. et al., "Effects Of The Mycelial Ectract Of The Cultured Cordyceps Sinenesis On in vivo Hepatic Energy Metabolism In The Mouse," Japanese Journal Of Pharmacoly, vol. 70, pp. 85–88 (1966).

Tsunoo, A. et al., "Cordyceps Sinensis: Its Diverse Effects On Mammals in vitro and in vivo," New Initiatives In Mycological Research, (1995).

Liu et al., "The Influence Of Cordyceps Sinensis (Berk.) Sacc. And Its Cultured Mycelia On Murine Platelets And Immune Organs After Irradiation With Cobalt–60 Gamma–Rays," Biological Abstracts, vol. 87, Abstract No. 8501, 1989.

China Abstract, CN 1 069 658, "Ahshan Health Beverage Product", Mar. 10, 1993.

China Abstract, CN 1 075 067, "Chen Shunziah", Aug. 11, 1993.

Inagawa et al. Chem. Pharm. Bull., vol. 40, No. 4, pp. 994–997, 1992.

Inagawa et al. Chem. Pharm. Bull., vol. 40, No. 4, pp. 998–1000, 1992.

*Primary Examiner*—Leon B. Lankford, Jr.
*Assistant Examiner*—Christopher R. Tate
*Attorney, Agent, or Firm*—Browdy and Neimark

[57] ABSTRACT

Secretion of gastric acid and development of ulcers can be inhibited by administering to a patient in need thereof an effective amount of a hot water extract of the cultivated mycelia of *Cordyceps sinensis*.

24 Claims, 4 Drawing Sheets

METHOD AND COMPOSITION FOR TREATING ULCERS AND SECRETION OF GASTRIC ACID

CROSS REFERENCE TO RELATED APPLICATIONS

This application is a division of co-pending parent application Ser. No. 08/777,110, filed Dec. 30, 1996; which is a continuation-in-part of PCT/JP95/01298 filed Jun. 29, 1995. The entire contents of both applications are hereby incorporated by reference.

FIELD OF THE INVENTION

The present invention relates to a method for treating ulcers and secretion of gastric acid comprising administering a pharmaceutical compositions derived from vegetative wasps.

BACKGROUND OF THE INVENTION

Vegetative wasps, e.g., plant worms, are fungi of Scoymycota, Pyrenomycetes, Clavicipitales, Clavicipitaceae, and Cordyceps. These wasps undergo both a complete metamorphic phase and an incomplete metamorphic phase. The fruits on which these fungi are found have been valued from ancient times as drugs which are effective for imparting perennial youth and longevity or for nourishment and tonicity. The fruit bodies which bear vegetative wasps that have heretofore been considered extremely valuable as Chinese medicinals are generally powdered and administered as powders.

According to the present invention, the mycelia of particular vegetative wasps are cultivated, and the thus-cultivated mycelia are extracted with hot water. The fact that the resulting extract from such mycelia has a cardiotonic and anti-fatigue effect, as well as an anti-ulcer effect, has heretofore been completely unknown.

SUMMARY OF THE INVENTION

The present invention provides agents and methods for treating ulcers and gastric acid secretion. These agents can be incorporated in foods and drinks and can be administered over long period of time without serious concern for safety.

Having investigated in order to attain the above-mentioned objects, the present inventors have specifically noted Chinese medicinals and vegetative wasps, especially those of *Cordyceps sinensis* and further studied them. As a result, we have found that the mycelia obtained by cultivating these vegetative wasps, especially the products obtained by extracting the cultivated mycelia with hot water, have mild cardiotonic, anti-ulcer and gastric secretion, and anti-fatigue effects. On the basis of this finding, we have further studied and have at last achieved the present invention. The present invention is described in detail hereunder.

BRIEF DESCRIPTION OF THE DRAWINGS

FIG. 4-1 shows the intake of $^3$H-thymidine in the primary culture heptaocytes of a rat.

FIG. 4-2 shows the intake of $^{14}$C-valine in the primary culture hepatocytes of a rat.

DETAILED DESCRIPTION OF THE INVENTION

To carry out the present invention, it is necessary to cultivate the mycelia of vegetative wasps of *Cordyceps sinensis* and to collect the thus-cultivated mycelia. All fungi of *Cordyceps sinensis* can be used in the present invention, and these will be referred to as the fungi of the invention. For example, *Cordyceps sinensis* MF-20008 has been found to be effective, and this strain has been deposited in the National Institute of Bioscience and Human Technology of the Agency of Industrial Science and Technology under the accession number FERM BP-5149.

According to the present invention, the mycelia of *Cordyceps sinensis* are cultivated in a medium comprising malt extract, yeast extract, peptone, potato broth, glucose, vitamins, amino acids, nucleic acids, proteins, and optional host components such as insects, etc., in a liquid or solid culture. The mycelia are thus fully propagated.

Liquid culture, especially stirring culture by aeration, is preferred for cultivating a large amount of the mycelia, which is conducted at pH of from 4 to 7 and at from 15 to 32° C., preferably from 20 to 30° C., while gently stirring the medium at approximately from 50 to 500 rpm, preferably from 100 to 300 rpm, for three to ten days.

After the culture, the thus-cultivated mycelia are extracted with hot water. Water is added to the mycelia, and these are, optionally after having been ground, heated at from 60 to 100° C., preferably from 85 to 100° C., more preferably from 90 to 95° C., and thus extracted with the hot water, optionally with stirring. The amount of water to be added is not specifically defined, but is preferably from 1 ml to 1 liter, per gram of the dry mycelia.

The residual substances are removed from the thus-obtained hot water extract, and the resulting liquid extract is used directly or after having been further processes, as the active ingredient of the present invention. The products obtained by processing the liquid extract broadly include a concentrated product, a paste product, a dried product, and/or a diluted product of the liquid extract. As the case may be, the hot water extract or its processed products may by used directly, without removing the residual substances therefrom, for example, as foods and drinks.

The hot water extract, including its processed products, or the mycelia has mild cardiotonic, hypotensive, antitussive and anti-fatigue effects. Compositions containing the hot water extract of the mycelia can be used as foods and drinks having these effects, foods and drinks for particular health, healthful drinks, healthful foods, nutritious foods, and other various types of foods and drinks, as well as medicines such as cardiac medicines, hypotensors, antitussives, tonics, etc.

For compositions comprising foods and beverages, the active ingredient of the hot water extract or its processed product may be used directly or may be combined with other foods or food components by conventional methods. The compositions of the present invention containing the active ingredient may be in any form such as a solid, including powder, granules, etc., paste, liquid, and suspension, and may be suitably formulated into nutritious beverages along with sweeteners, acidifiers, vitamins, and other various additives for conventional beverages.

For medicinal compositions, the active ingredient may be administered in a variety of forms. These forms include oral compositions, including, for example, tablets, capsules, granules, powders, syrups, etc. These preparations can be formulated by conventional methods with known auxiliary additives which are generally used in formulating pharmaceuticals, such as vehicles, binders, disintegrators, lubricants, flavorings, dissolution aids, suspending agents, coating agents, etc. The dose of the active ingredient to be administered varies, depending on the condition, the age, and the weight of the person to which it is administered, as well as on the route of administration and the form of the preparation. The active ingredient is generally administered from 0.1 mg/adult to 1000 mg.adult for one dose.

The active ingredient of the present invention is obtained from natural products which have been used for many years as Chinese medicines, and is completely non toxic or is only slightly toxic. Therefore, the active ingredient of the present invention is safe. In oral administration to rats a dose of 500 mg. a day resulted in no acute toxicity. Therefore, the amount of the active ingredient to be incorporated in food or beverage compositions is not specifically limited by use, whether for preventing disease, preserving health, and ordinary use. For pharmaceutical compositions, the amount of the active ingredient to be included therein may be defined within the above-mentioned range in accordance with the patients' needs. Since the active ingredient of the present invention exhibits no toxicity even when a large amount of it is administered, the dose to be administered my be over the above-mentioned range, if desired, with no problem.

PRODUCTION EXAMPLE 1

One liter of M20Y2 medium (comprising 20 g of malt extract (Oxoid) and 2 g of yeast extract (Difco) in one liter and having a pH of 5.5) was put into each of 46 3-liter Erlenmeyer flasks, which were then sterilized in an autoclave at 121° C. for 15 minutes.

One platinum loop of the mycelia of *Cordyceps sinensis* MF-20008 (obtained from The Sanming Mycological Instituted, Fujian, China), FERM BP-5149, that had been pre-cultivated by M20Y2 agar slant culture was inoculated in each sterilized medium and cultivated therein at 25° C. by shaking culture at 180 rpm for 5 days. Thus, 46 liters of the culture was obtained in these 46 flasks.

46 liters of the culture were centrifuged, and the mycelia thus separated were freeze-dried to obtain 323.6 g of dry mycelia. The dry mycelia were put into a stainless container, 7 liters of water were added thereto, and these were ground with a polytoron, heated at from 90 to 95° C. for 2 hours while stirring, and then extracted. After the extraction, the residual substances were removed by filtration, and the resulting filtrate was freeze-dried to obtain 130 g of a lightly yellow powder.

PRODUCTION EXAMPLE 2

In the same manner as in Production Example 1, 150 ml M20Y2 medium was put into a 500-ml Erlenmeyer flask and sterilized by autoclaving, and 1 ml of freeze-dried *Cordyceps sinensis* MF-20008 was inoculated therein and cultivated by shaking culture at 25° C. and 180 rpm for 5 days. This was used as a seed culture and cultivated in 150 liters of the following medium in the manner described below.

150 liters of D medium (comprising 40.0 g of sucrose, 4.0 g of $K_2HPO_4$, 0.5 G OF asparagine, 2.0 g of $(NH_4)_2HPO_4$, 2.0 g of $MgSO_4 \cdot 7H_2O$, 0.25 g of $CaCO_3$, 0.1 g of $CaCl_2$ and 4.0 g of yeast extract B-2 in one liter and having pH of 5.6) was sterilized and filtered and then put into a 150-liter fermenter. 150 ml of the above-mentioned seed culture was inoculated therein and cultivated under controlled conditions at 25° C., pH of 5.5 and DO of 50%, with stirring at 157 rpm, for 3 days. The foams formed during the cultivation were removed by adding a silicone de-foaming agent to the fermenter. 150 liters of the culture thus obtained was treated with a clarifier to thereby isolate the mycelia. An aqueous suspension of the mycelia was obtained. This was heated at from 90° C. to 95° C. for 2 hours and extracted. Then this was clarified with a clarifier to isolate a supernatant. This was filtered through $0.45\mu$ and $0.22\text{-}\mu m$ sterile filters to obtain 80 liters of a light yellow hot-water extract (the dry weight of the solid content: 800 g).

EXAMPLE 1

The cultivated mycelia (dry mycelia) of *Cordyceps sinensis* MF-20008 that had been prepared in Production Example 1 and the hot-water extract thereof (lightly yellow powder) were subjected to a swimming fatigue test with mice, to which the cultivated mycelia and the hot-water extract thereof were orally administered.

The test animals were male ICR mice (5 to 7 week-age), and these were grouped into three groups and subjected to a fatigue test under the conditions mentioned below.

Administration

The hot-water extract of the mycelia of *Cordyceps sinensis* MF-20008 or the mycelia themselves were mixed with powdery CRF-1 feed at a proportion of 2.5% of 5%, respectively, and the resulting powdery feed mix was administered to the mice all the time for 16 days.

Group of Mice

Each group was comprised of 20 mice.

(1) Control group: Fed with only powdery CRF-1 feed.

(2) Group to which the hot-water extract was administered: Fed with the feed mix containing 2.5% of the the hot-water extract, (3) Group to which the mycelia were administered: Fed with the feed mix containing 5% of the dry mycelia.

Test Schedule

On the 15th day after the start of the administration, the mice were subjected to a swimming fatigue test. On the 16th day, all the blood collected from each mouse and subjected to whole blood analysis and serum analysis.

(1) The swimming fatigue test is as follows: A 36-liter swimming tank (49 cm×33.5 cm×22 cm (depth)) was filled with water at 17° C., and 10 ml of neutral detergent was added thereto. The mice were forced to swim in the tank under no load, and the swimming test for each mouse was stopped at the time at which the mouse sank in water up to the tip of its nose for 5 seconds. The results obtained are shown in Table 1 below.

TABLE 1

| | Gauge No. | | | |
|---|---|---|---|---|
| No. | 1 | 2 | 3 | 4 |
| Group (1) (Control) | | | | |
| 1 | 9' 55" | 7' 06" | 7' 41" | 10' 34" |
| 2 | 8' 57" | 6' 14" | 9' 08" | 12' 10" |
| 3 | 7' 54" | 8' 45" | 7' 34" | 8' 24" |
| 4 | 8' 28" | 7' 37" | 8' 54" | 8' 08" |
| 5 | 9' 28" | 9' 09" | 9' 42" | 10' 40" |

TABLE 1-continued

| | | Gauge No. | | |
|---|---|---|---|---|
| No. | 1 | 2 | 3 | 4 |

Group (2) (Fed with the feed mix containing the hot-water extract of the cultivated mycelia)

| | | | | |
|---|---|---|---|---|
| 1 | 9' 16" | 12' 33" | 11' 22" | 9' 56" |
| 2 | 6' 36" | 11' 04" | 11' 43" | >15' 00" |
| 3 | 11' 51" | 7' 35" | 10' 37" | 11' 33" |
| 4 | 10' 45" | >15' 00" | 10' 02" | 9' 25" |
| 5 | 12' 04" | 9' 33" | >15' 00" | 7' 40" |

Group (3) (Fed with the feed mix containing the cultivated mycelia)

| | | | | |
|---|---|---|---|---|
| 1 | 12' 32" | 7' 51" | 9' 53" | 10' 54" |
| 2 | 9' 00" | 6' 33" | >15' 00" | 12' 18" |
| 3 | Died | 9' 07" | 7' 28" | 10' 49" |
| 4 | 11' 34" | 8' 59" | 13' 08" | 7' 19" |
| 5 | 9' 10" | 7' 40" | 7' 26" | 8' 02" |

The above-mentioned results were analyzed by the Aspin-Welch test of significance. There was a significant difference between the first group and the second group, as the level of significance of the test was 1%. However, there was no significant difference between the first group and the third group, as the level of significance of the test was 5%.

The swimming fatigue test is one of the tests which generally employed for the purpose of evaluating the ant-fatigued effect of test substances on the basis of the variation in the total reaction of test animals. Therefore, above-mentioned results have scientifically verified the excellent effect of the active ingredient of the present invention for increasing the sustaining capacity for power of locomotion and the excellent anti-fatigue effect of the same.

(2) On the 16th day after the start of the administration, whole blood was collected from each mouse that had been subjected to the above-mentioned swimming fatigued test and analyzed in terms of the number of the platelets ($\times 10,000/mm^3$), the number of leucocytes ($/mm^3$), and the hematocrit (%).

The results of the analysis of the whole blood are shown in Table 2 below. As is obvious from these results, there was no significant difference between the test groups and the control group in all the test items, as the level of significance of the test was 5%. (to analyze the whole blood, a Student test was used. To count the number of the platelets in the third group, however, and Aspin-Welch test was used.)

TABLE 2

| No. | Number of Platelets × $10000/mm^3$ | Amount of Hemoglobin g/dl | Number of Erythrocytes × $10000/mm^3$ | Number of Leucocytes/$mm^3$ | Hematocrit % |
|---|---|---|---|---|---|
| First Group (Control Group) | | | | | |
| 1 | 106.5 | 14.5 | 879 | 4300 | 55.1 |
| 2 | 130.5 | 15.5 | 984 | 4200 | 57.9 |
| 3 | 107.5 | 16.3 | 1075 | 3600 | 59.2 |
| 4 | 120.1 | 16.4 | 1104 | 5700 | 58.5 |
| 5 | 109.4 | 15 | 963 | 6300 | 58.6 |
| 6 | 95.8 | 15.5 | 984 | 5100 | 59.5 |
| 7 | 108.4 | 14.5 | 898 | 2700 | 57.5 |
| 8 | 89.4 | 15 | 943 | 4400 | 55.5 |
| 9 | 114.4 | 15 | 1065 | 4600 | 57.8 |
| Average | 109.11 | 15.41 | 988.33 | 4544.44 | 57.73 |
| Second Group (Fed with Hot-water Extract of Cultivated Mycelia of MF-20008) | | | | | |
| 1 | 102.6 | 15 | 939 | 4500 | 56.7 |
| 2 | 121.8 | 14.7 | 923 | 5900 | 52.6 |
| 3 | 136.1 | 14.5 | 869 | 5200 | 56.4 |
| 4 | 97.7 | 14.5 | 866 | 4800 | 53.6 |
| 5 | 77.1 | 16.4 | 1011 | 4200 | 58 |
| 6 | 119 | 15.3 | 932 | 6400 | 56.5 |
| 7 | 107.8 | 13.7 | 863 | 4000 | 50.7 |
| 8 | 100.8 | 16.2 | 1016 | 4400 | 58.9 |
| 9 | 121 | 15.7 | 1004 | 5800 | 56.3 |
| 10 | 128 | 16.1 | 1015 | 5000 | 57.9 |
| Average | 111.19 | 15.21 | 943.8 | 5020 | 55.76 |
| Third Group (Fed with Dry Mycelia of MF-20008) | | | | | |
| 1 | 88.3 | 13.7 | 835 | 7000 | 51 |
| 2 | 97.6 | 15.9 | 994 | 3200 | 56.3 |
| 3 | 103.6 | 15.3 | 916 | 3300 | 55.3 |
| 4 | 116 | 14.7 | 951 | 7000 | 56.7 |
| 5 | 155.7 | 15.5 | 936 | 7000 | 57.4 |
| 6 | 131.6 | 15.2 | 943 | 4100 | 56.6 |
| 7 | 119.3 | 16.6 | 1010 | 4700 | 59.3 |
| 8 | 130.9 | 16.2 | 991 | 5200 | 57.9 |
| 9 | 113.1 | 15.7 | 1026 | 7700 | 58.8 |
| 10 | 58.6 | 15.8 | 994 | 6400 | 57.4 |
| Average | 111.47 | 15.46 | 959.6 | 5560 | 56.67 |

(3) Each test mouse was weighed during the period of the test, and the variation in the mean weight (g) of the test mice is shown in Table 3 below (Variation in Weight of Mice Treated by Forced Swimming Test).

TABLE 3

| Days after the Start of Administration | Mean Body Weight (g) | | |
|---|---|---|---|
| | 1st Group | 2nd Group | 3rd Group |
| 0 | 32.19 | 32.24 | 32.14 |
| 2 | 33.74 | 33.94 | 33.75 |
| 4 | 34.18 | 34.37 | 34.30 |
| 7 | 35.38 | 35.25 | 35.02 |
| 10 | 35.81 | 35.66 | 35.99 |
| 14 | 36.68 | 37.52 | 36.67 |
| 16 | 38.30 | 38.41 | 37.64 |

EXAMPLE 2

The hot-water extract of the mycelia of *Cordyceps sinensis* MF-20008 that ha been prepared in Production Example 1 was tested in terms of its effects on the right atrium, the papillary muscle of the right ventricle, the aorta and the bronchi removed from an SD rat, according to a Tsunoo et al's method (see Kurokawa M. Tsunoo A., J. Physiol., 407, 135–153, 1988; Tsunoo A. et at., J. Physiol., 433, 163–181, 1991), and the effectiveness of the extract was evaluated.

(1) Specimen of Cardiac Muscle

By applying the hot-water extract to the specimen of the cardiac muscle of a male SD rat, the contractile force of the cardiac muscle of the right atrium and the inter-contraction interval thereof were measured.

The right atrium with intact pacemaker activity was removed from a male SD rat (380 to 450 g). The specimen of the right atrium was fixed in a horizontal perfusion container having a volume of 0.8 ml., and its contractile force was isometrically recorded. As the perfusate, a Krebs solution was used that had been equilibrated with 95% oxygen and 5% carbon dioxide, or aerated salt solution comprising 140 mM of sodium chloride, mM of potassium chloride, 2.6 mM of calcium chloride, 1.3mM of magnesium Chloride, 10 mM of glucose and 5 mM of HEPES. The perfusate was kept at from 36 to 37° C. and at a flow rate of from 3 to 4 ml/min.

Figure 1:
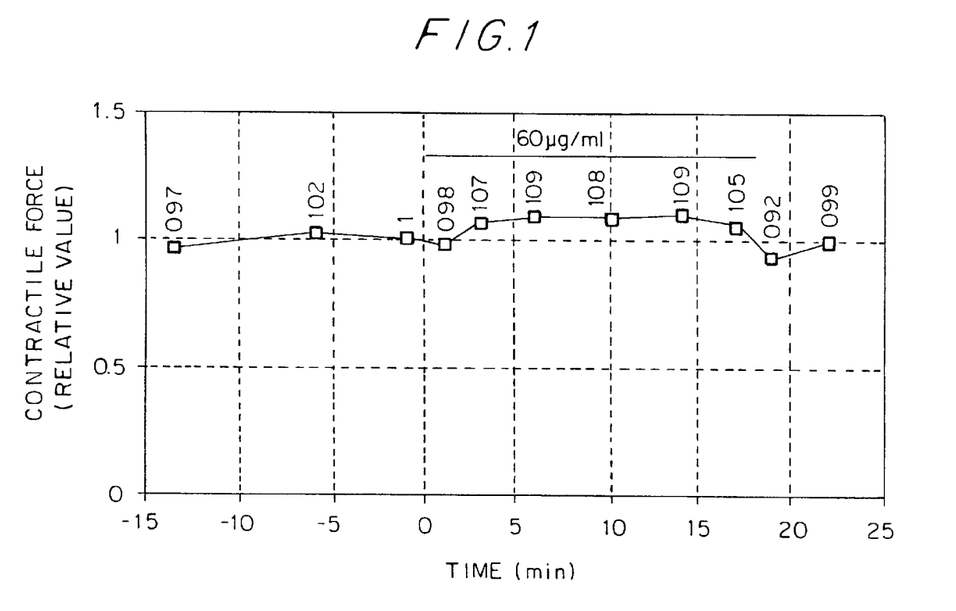
FIG. 1 shows the effect of a hot water extract of the mycelia of *Cordyceps sinensis* MF-20008 on the contractile force of the right atrial muscle of a rat.
Figure 2:
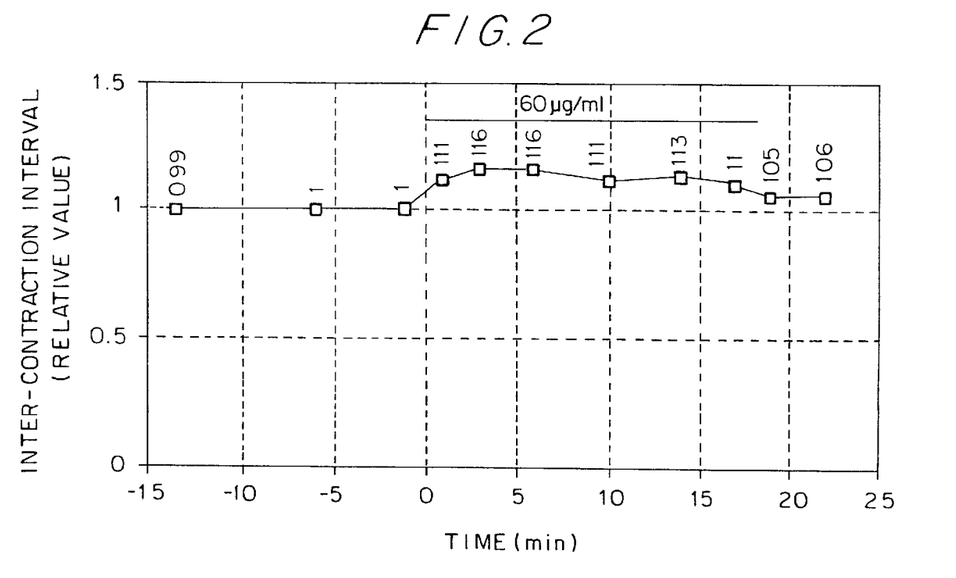
FIG. 2 shows the effect of a hot water extract of the mycelia of *Cordyceps sinensis* MF-20008 on the inter-contraction interval of automatic contractions of the rat right atrium.

As a result, the hot-water extract of the mycelia (from 50 100 $\mu$g/ml) increased the contractile force of the cardiac muscle of the right atrium by 9±3% of the control (mean value±standard deviation, n=5). The interval of the pacemaker-driven spontaneous contractions was prolonged by 14±10% of the control (n=4). FIG. 1 and FIG. 2 show the time course of increase in the contractile force of the cardiac muscle of the right atrium and the time course of prolongation of the inter-contraction interval of the same, respectively.

In FIGS. 1 and 2, the extract solution (60 $\mu$g/ml) was applied to the test system during the period time expressed by the thick solid line. The vertical axis indicated the relative value of the contractile force relative to the standard value of the control (before application of the extract solution) of being 1 (one). The horizontal axis indicates the time, on which 0 (zero) means the time at which the extract solution was applied to the test system and the minus number means the time before the application.

As is obvious from the above, the effectiveness of the hot-water extract on the spontaneous contraction of the right atrium was verified by the illustrated data. In addition, the papillary muscle of the right ventricle was taken out of the rat and fixed in a perfusion container the same manner as above, to which was applied electric stimulation (2 Hz) via a pair of platinum wires, and the effectiveness of the extract on the electrically-driven contractions of the papillary muscle of the right ventricle was examined. As a result, the extract (from 30 to 100 $\mu$g/ml) increased the tension of the papillary muscle of the right ventricle to be caused by the electric stimulation by 13±1% of the control (n=3).

(2) Specimen of Aorta

By applying the hot-water extract to the specimen of the aorta of a male SD rat, the effect of the extract on the aorta and also the effect of the sustaining contraction of the aorta caused by 50 mM potassium were examined.

The aorta was removed from a male SD rat and formed into a spiral section specimen. The specimen was fixed in a perfusion container under the same conditions as above. The 50 mM potassium solution to be used for stimulating the specimen was prepared by substituting sodium chloride in the container by potassium chloride.

As a result, the hot-water extract of the mycelia (from 50 to 100 $\mu$g/ml) exhibited no significant effect on the aorta which was in a static condition. However, this relaxed the sustaining contraction of the aorta caused by 50 mM potassium. Where the contraction tension of the aorta caused by 50 mM potassium was referred to as 100%, the extract reduced the tension by from 2 to 12% (n=5).

(3) Specimen of Bronchi

By applying the hot-water extract to the specimen of the bronchi of a male SD rat, the effect of the extract of the contraction of the bronchi to be caused by electric stimulation or by 50 mM potassium was examined.

The bronchi were removed from a male SD rat and formed into a spiral specimen. The specimen was fixed in a perfusion container under the same conditions as above. The 50 mM potassium solution to be used for stimulating the specimen was prepared in the same manner as above. The electric stimulation was applied to the specimen at intervals of 30 seconds via a platinum wire set in the perfusion container.

As a result, the hot-water extract of the mycelia (from 50 to 100 $\mu$g/ml) inhibited the transient contraction of the bronchi caused by electric stimulation by from 23 to 65% of the control (n=3). This also relaxed the sustaining contraction of the bronchi caused by 50 mM potassium. Where the contraction tension of the bronchi caused by 50 mM potassium was referred to as 100%, the extract reduced the tension by from 9 to 13% (n=3). This was comparable to or more than the relaxing effect of theophylline (50 $\mu$M).

As is obvious from the results in the above-mentioned (1) to (3), it is believed that the hot-water extract of the mycelia has (1) a mild effect of enhancing the contractile force of the cardiac muscle, while prolonging the inter-contraction interval of the cardiac muscle, while prolonging the inter-contraction interval of the cardiac muscle, (2) the extract has a vasodilating effect, increasing the systemic blood flow, and (3) since the extract inhibits the transient and sustaining contraction of the bronchi, its lowers the airway resistance and increases the pulmonary ventilation. Thus, it has been confirmed from these scientific data that the composition of the present invention has a cardiotonic effect, a hypotensive effect and an antitussive effect.

EXAMPLE 3

Using the hot-water extract (freeze-dried powder) of the mycelia of *Cordyceps sinensis* MF-20008 that had been prepared in Production Example 1, a water-dipped, restrained stress ulcer test with rats was conducted to examine the anti-stress effect of the extract.

Test Animals

Five-week old, male Sprague-Dawley rats were bought from Nippon Charles River and pre-raised for about one week. The thus-raised six-week old rats were used as test animals.

Administration

The hot-water extract of the mycelia of *Cordyceps sinensis* MF-20008 was dissolved in distilled water for injection at a concentration of 50 mg/ml, and this was divided into plural parts each for one-day dose. These were frozen and stored at −20° C. Before use, these were thawed at room temperature. Distilled water for injection only was applied to the rats of the control group. The solution of the extract or the distilled water was orally administered to rats via a metal gastroprobe for rats. The dose of the active ingredient, the dose of the solution (or distilled water) and the administration schedule are shown in Table 4 below. The dose of the solution (or distilled water) was calculated on the basis of the newest body weight of each rat, and the administration was effected, as a rule, at from 9 to 12 in the morning.

TABLE 4

| Group | Dose of Active Ingredient (mg/kg/day) | Dose of Solution (or Distilled Water) (ml/kg/day) | Administration Schedule (2) | Number of Animals (heads) |
|---|---|---|---|---|
| Control | −(1) | 4 | day 0–4, 7–11 | 5 |
|  | 100 | 2 | day 0–4, 7–11 | 5 |
|  | 200 | 4 | day 0–4, 7–11 | 5 |

(1) Four ml/kg/day of distilled water for injection was administered to each rat of the control group.
(2) The day at which the administration was started was referred to as 0 (zero).

Water-dipped, Restrained Stress Ulcer Test (The Stress Was Applied on Days 10–11 Overnight):

For about 12 hours before the application of the water-dipped, restrained stress thereto, the rats were made to abstain from feed. After this, the rats were put into a stress gauge and dipped in water up to their xiphoid process. The time for the water-dipping restraint was 15 hours. After the application of the stress thereto, the rats were anesthetized and killed, and the stomach was taken out while ligating the upper portion of the cardiac part of the stomach and duodenum. A physiological saline solution was injected into the stomach, and the stomach was dipped in a formalin solution. After 15 minutes, the stomach was opened, and the length of the ulcer formed in the gastric mucosa was measured. After the measurement, the stomach was fixed with formalin and subjected to pathoanatomical inspection and the ulcer formed was scored according to the following criteria.

Score 0: No ulcer formed.
1: Ulcer formed in the upper portion of the mucosa.
2: Ulcer formed in the lamina propria mucosa.
3: Ulcer formed in the lamina muscularis mucosa.
4: Ulcer formed in the tunica serosa ventriculi.

Figure 3:
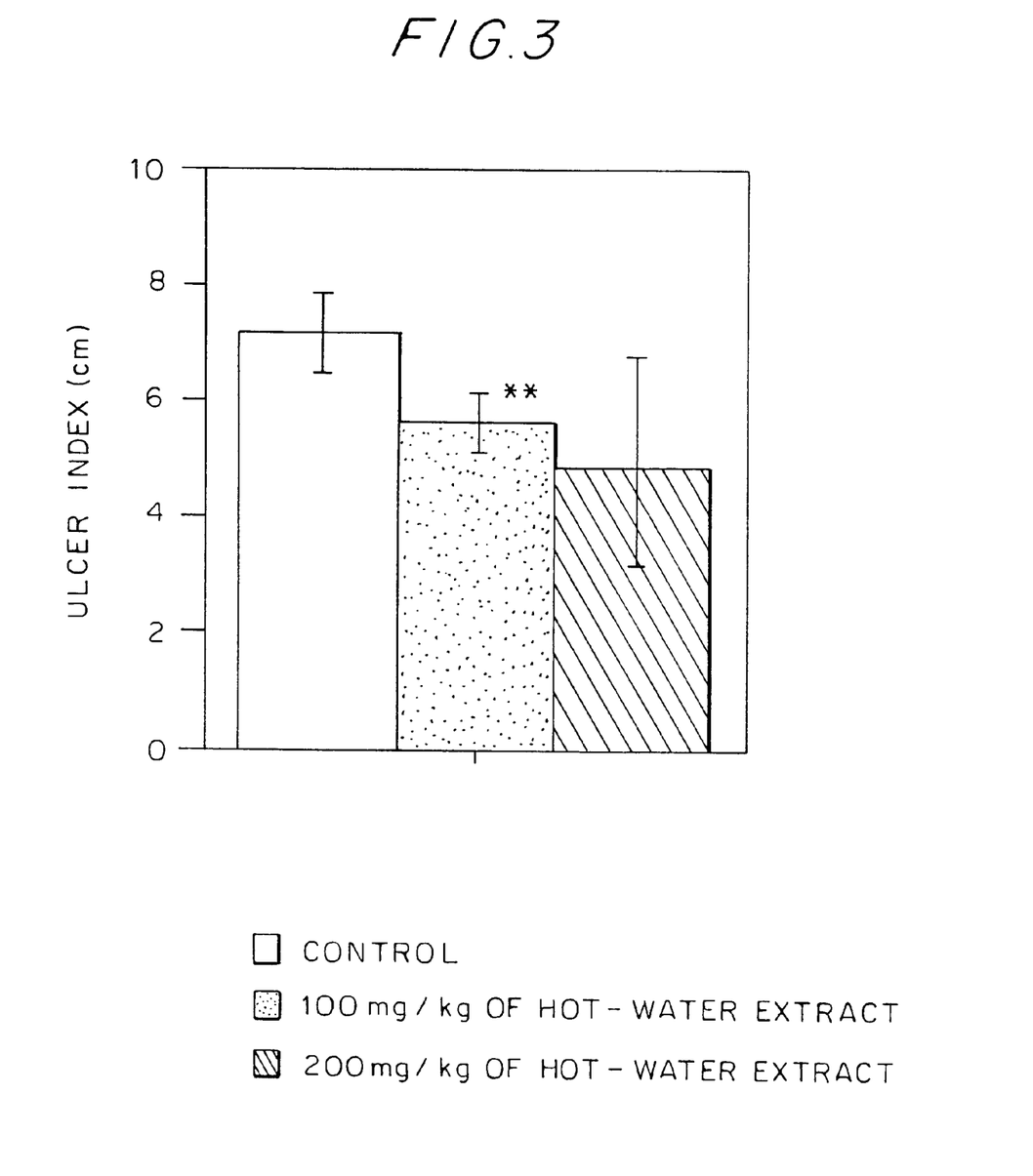
FIG. 3 shows the ulcer index (cm) of the ulcer formed in the gastric mucosa of a rat, to which a hot water extract of the mycelia of *Cordyceps sinensis* MF-20008 was administered.
Figure 4A:
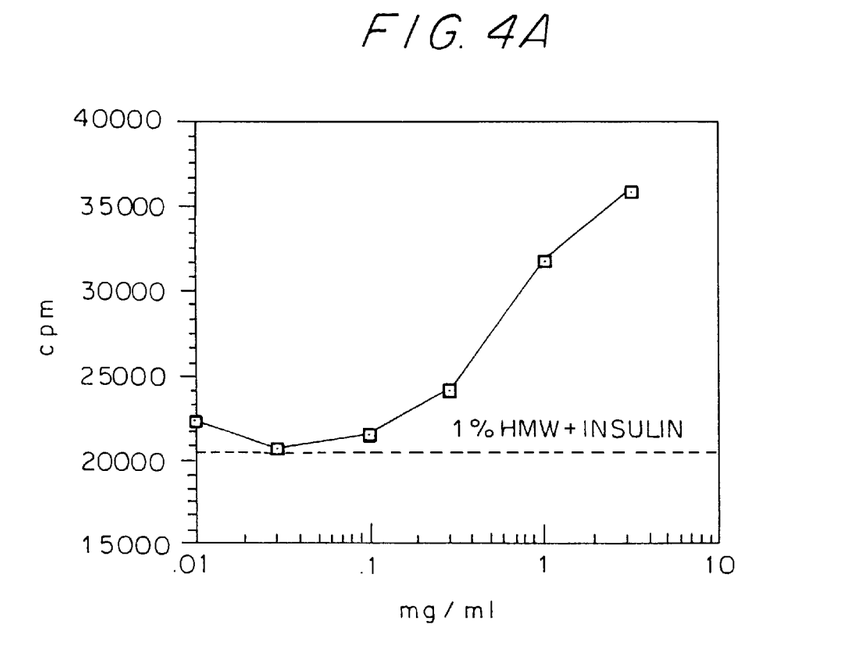
Figure 4B:
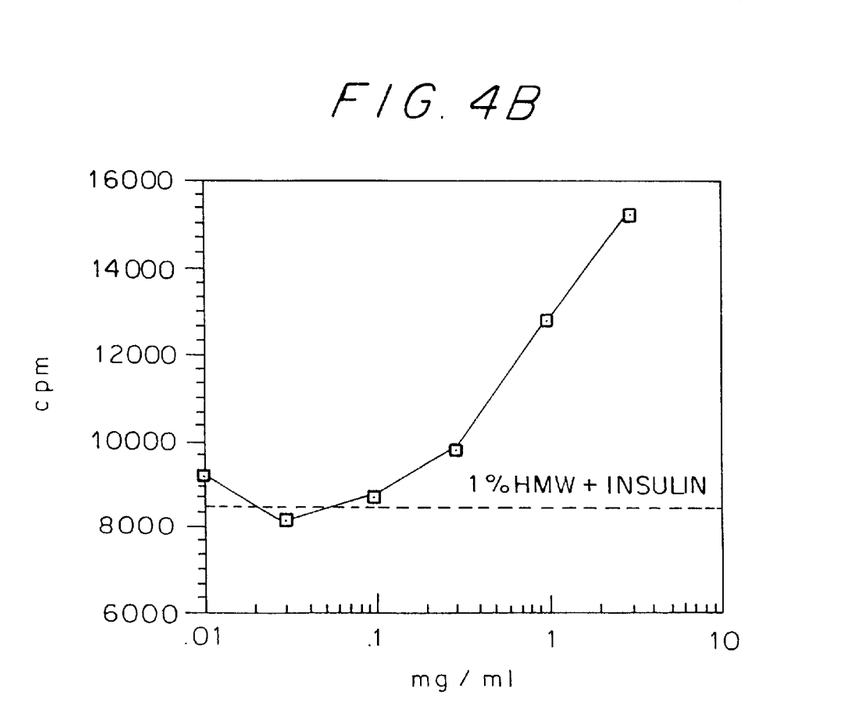

The results are shown in FIG. 3 and Table 5.

TABLE 5

| Ulcer Index | | Microscore of Gastric Ulcer |
|---|---|---|
| Control | 1 | 1 |
|  | 2 | 2 to 3 |
|  | 3 | 2 |
|  | 4 | 2 to 3 |
|  | 5 | 3 |
|  | Average | 2.4 |
| 100 mg/ml of extract of mycelia of *Cordyceps sinensis* MF-20008 applied. | 1 | 2 to 3 |
|  | 2 | 1 |
|  | 3 | 0 |
|  | 4 | 1 to 2 |
|  | 5 | 1 |
|  | Average | 1.4 |
| 200 mg/ml of extract of mycelia of *Cordyceps sinensis* MF-20008 applied. | 1 | 1 |
|  | 2 | 1 |
|  | 3 | 2 |
|  | 4 | 2 |
|  | 5 | 3 |
|  | Average | 1.8 |

EXAMPLE 4

As one index of the anti-fatigue effect of the hot-water extract of the cultivated mycelia of *Cordyceps sinensis*, the activity of the extract on the promotion of the DNA synthesis and the protein synthesis in the primary culture hepatocytes of a rat was examined.

Preparation of an extract containing a hepatocytes growth factor derived from a bovine small intestinal epitheliomucosa and characteristics of the extract:

A methanol-soluble extract of a bovine small intestinal epitheliomucosa consists essentially of low-molecular substances as estimated by gel permeation chromatography, and it is referred to as a low-molecular weight fraction (LMW). On the other hand, an extract to be obtained by extracting a bovine small intestinal epitheliomucosa with methanol followed by further extracting the resulting residue with PBS consists essentially of proteinaceous high-molecular weight substances, and it is referred to as a high-molecular weight fraction (HMW).

When LMW is added to the primary culture hepatocytes of a rat, it promotes the DNA and protein synthesis in the presence of insulin in the cells. When a combination of LMW and HMW is added thereto, the DNA and protein synthesis is additively accelerated compared to the basic activity of HMW. In other words, LMW exhibits the essential activity in this assay system, while HMW has an additive activity. The hot-water extract of *Cordyceps sinensis* comprising a low-molecular weight fractions based on the extraction process. The extract was added to the primary culture hepatocytes of a rat in the presence of 1% HMW and 1×10−7 M insulin, and the effect of the extract of promoting the DNA and protein synthesis in these cells was examined on the basis of the intake of $^3$H-thymidine and $^{14}$C-valine in the cells.

Results

When the hot-water extract of the mycelia of *Cordyceps sinensis* was added to the primary culture hepatocytes of a rat in the presence of insulin and HMW, it obviously promoted the synthesis of DNA protein in the cells. The results are shown in FIG. 4-1 and FIG. 4-2. However, in the absence of insulin and HMW, any significant activity of the extract was not detected. In the presence of only insulin, the activity of the extract was not also detected. From these, it is believed that extract promotes the synthesis of DNA and protein the cells in the presence of insulin and HMW.

EXAMPLE 5

The hot-water extract of the mycelia of *Cordyceps sinensis* MF-20008 that had been prepared in Production example 1 was administered to rats, and the effect of the extract of retarding the secretion of the gastric acid in the rats was examined.

In this test, healthy, male SD rats were used (Nippon Charles River Co.); the five-week old rats had been purchased and further pre-raised for 4 days and then used for the test. The rats were grouped in two groups, a test group and a control group, each being comprised of 4 rats. To the rats o the test group, the hot-water extract of the mycelia of *Cordyceps sinensis* MF-20008 was administered.

The hot-water extract of the mycelia of *Cordyceps sinensis* MF-20008 was dissolved in pure water (Lot No. YULE9566, produced by Wako Pure Chemicals Co.) at a concentration of 100 mg/ml to prepare a test material to be administered to the rats, and this was frozen and stored.

Pure water or the test material having predetermined concentration was orally administered to the rats via a metal gastroprobe, at 9 in the morning every day. On the 12th day, it was injected into the duodenum after the pylorus had been ligated.

| Group | Number of Animals Administered (heads) | Substance Administered | Dose (mg/kg/day) | Administration Route | Administration Schedule |
|---|---|---|---|---|---|
| Control Group | 4 | Pure Water | — | Oral Administration | 1 to 11 days |
| Test Group (extract administered) | 4 | Test Material | 200 | Oral Administration | 1 to 11 days |

The secretion of the gastric juice was measured in the manner described below.

The rats were made to abstain from feed for 17 hours. After this, while they were anesthetized, the abdomen was opened and the pylorus portion was ligated. After 4 hours, the rats were killed by dislocation of cervical vertebrae, their stomachs were removed, and the gastric juice which remained therein was collected. The thus-collected gastric juice was subjected to centrifugation at 3,000 rpm for 5 minutes. The volume of the gastric juice (ml/rat), the acidic degree of the gastric juice (mEq/liter) and the pH thereof were measured. The acidity was measured up to pH 7.0 with a pH meter using 0.01 N NaOH. From the volume of the gastric juice and the acidic degree thereof thus measured, the amount of the acid released per hour ($\mu$Eq/hr) was calculated. The test material was injected into the duodenum immediately after the ligation of the pylorus.

Figure 5:
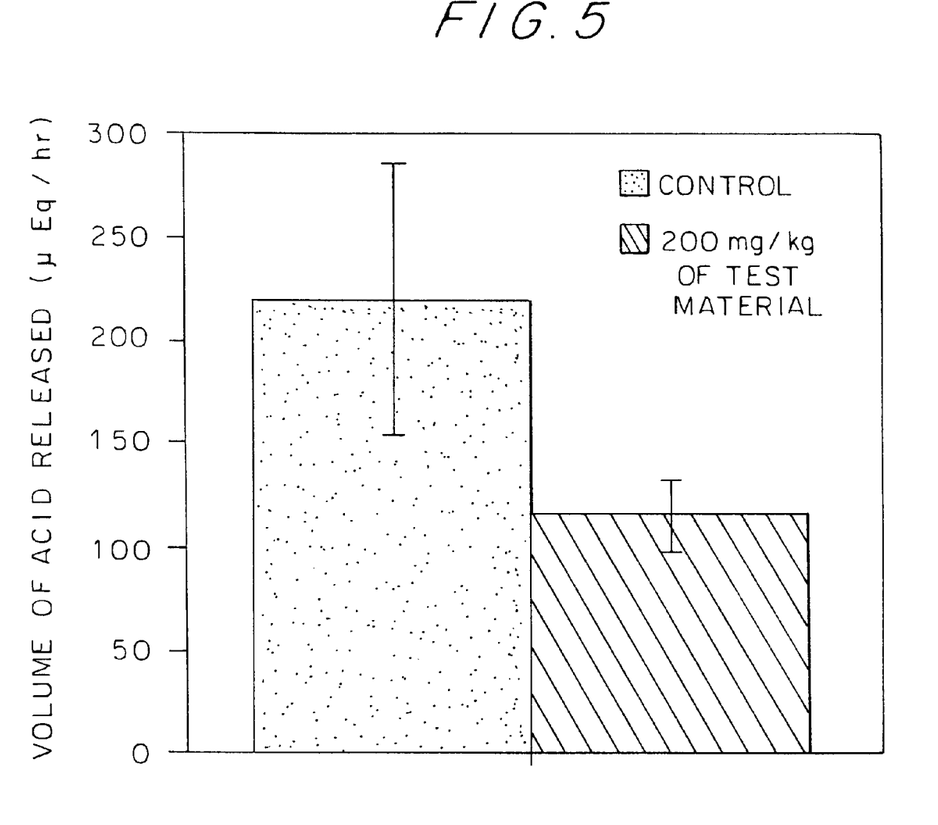
FIG. 5 shows the effect of a hot water extract of the mycelia of *Cordyceps sinensis* MF-20008 for the inhibition of the gastric acid secretion in a rat.

The results are shown in FIG. 5.

EXAMPLE 6

Water was added to 100 g of the powder of the hot-water extract obtained in Production Example 1, 150 g of saccharides, 15 g of honey, 1 g of ascorbic acid, 0.5 g of citric acid and a suitable amount of fragrance to make on kg as a whole. This was sterilized at 95° C. for 20 minutes and filled in bottles in an amount of 100 ml each in a germ-free condition. Thus, a healthful drink was prepared.

EXAMPLE 7

De-ionized water was added to 200 g of an aqueous 20% solution of the powder of the hot-water extract obtained in Production Example 1, 5 g of tocopherol acetate, 10 g of thiamine nitrate, 20 g of nicotinic acid amide, 50 g of anhydrous caffeine and suitable amounts of benzoates and fragrance to make 30 liters as a whole. After being sterilized, 30 ml of this beverage was introduced into sterile bottles. Thus, a medicine-type healthful drink was prepared.

EXAMPLE 8

| | |
|---|---|
| (1) Substance prepared in Production Example 1 | 50 g |
| (2) Lactose | 90 g |
| (3) Corn starch | 29 g |
| (4) Magnesium stearate | 1 g |

(1), (2) and (3) (17 g) were mixed and granulated along with a paste formed from (3) (7 g). (3) (5 g) and (4) were added to the thus-obtained granules and well mixed, and the resulting mixture was tabletted under pressure, using a compression tabletting machine, to obtain 1000 tablets each containing 50 mg of the active ingredient (1).

ADVANTAGES OF THE INVENTION

According to the present invention, there is provided a composition derived from a natural substance which is extremely stable and has mild cardiotonic, hypotensive, antitussive and anti-fatigue effects. Though being derived from natural substances, it is possible to stably and industrially provide the composition by culture.

Reference to Deposited Microorganisms under Rule 13-2
1. MF-20008
  a. Name and Address of the Authorized Depository for Deposition of the Present Microorganisms; Name: The National Institute of Bioscience and Human-Technology of the Agency of Industrial Science and Technology of the Ministry of International Trade and Industry, Japan Address: Higashi 1 chome, Tsukuba-shi, Ibaraki-ken 305, Japan
  b. Date of Deposition in the Depository of a: Jun. 29, 1994
  c. Deposition Number as Rendered by the Depository a: FERM BP-5149

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A method for inhibiting the development of ulcers in a patient in need thereof comprising administering to said patient an effective amount of a composition comprising a hot-water extract of the cultivated mycelia of *Cordyceps sinensis* wherein the extract does not contain extraction residue and the extract is in the form of a member selected from the group consisting of liquid, paste, and dry solid.

2. The method according to claim 1, wherein the hot water extraction was carried out at a temperature range of from 85 to 100° C.

3. The method according to claim 2, wherein the hot water extraction was carried out at a temperature range of from 90 to 100° C.

4. The method according to claim 1, wherein the *Cordyceps sinensis* is *Cordyceps sinensis* MF-20008.

5. The method according to claim 2, wherein the *Cordyceps sinensis* is *Cordyceps sinensis* MF-20008.

6. The method according to claim 3, wherein the *Cordyceps sinensis* is *Cordyceps sinensis* MF-20008.

7. A method for inhibiting the development of ulcers in a patient in need thereof comprising administering to said patient an effective amount of a composition comprising a hot-water extract of the cultivated mycelia of *Cordyceps sinensis* wherein the extract contains extraction residue and the extract is in the form of a member selected from the group consisting of liquid, paste, and dry solid.

8. The method according to claim 7, wherein the hot water extraction was carried out at a temperature range of from 85 to 100° C.

9. The method according to claim 8, wherein the hot water extraction was carried out at a temperature range of from 90 to 100° C.

10. The method according to claim 7, wherein the *Cordyceps sinensis* is *Cordyceps sinensis* MF-20008.

11. The method according to claim 8, wherein the *Cordyceps sinensis* is *Cordyceps sinensis* MF-20008.

12. The method according to claim 9, wherein the *Cordyceps sinensis* is *Cordyceps sinensis* MF-20008.

13. A method for retarding the secretion of gastric acid in a patient in need thereof comprising administering to said patient an effective amount of a composition comprising a hot water extract of the cultivated mycelia of *Cordyceps sinensis* wherein the extract does not contain extraction residue and the extract is in the form of a member selected from the group consisting of liquid, paste, and dry solid.

14. The method according to claim 13, wherein the hot water extraction was carried out at a temperature range of from 85 to 100° C.

15. The method according to claim 14, wherein the hot water extraction was carried out at a temperature range of from 90 to 100° C.

16. The method according to claim 13, wherein the *Cordyceps sinensis* is *Cordyceps sinensis* MF-20008.

17. The method according to claim 14, wherein the *Cordyceps sinensis* is *Cordyceps sinensis* MF-20008.

18. The method according to claim 15, wherein the *Cordyceps sinensis* is *Cordyceps sinensis* MF-20008.

19. A method for retarding the secretion of gastric acid in a patient in need thereof comprising administering to said patient an effective amount of a composition comprising a hot water extract of the cultivated mycelia of *Cordyceps sinensis* wherein the extract contains extraction residue and the extract is in the form of a member selected from the group consisting of liquid, paste, and dry solid.

20. The method according to claim 19, wherein the hot water extraction was carried out at a temperature range of from 85 to 100° C.

21. The method according to claim 20, wherein the hot water extraction was carried out at a temperature range of from 90 to 100° C.

22. The method according to claim 19, wherein the *Cordyceps sinensis* is *Cordyceps sinensis* MF-20008.

23. The method according to claim 20, wherein the *Cordyceps sinensis* is *Cordyceps sinensis* MF-20008.

24. The method according to claim 21, wherein the *Cordyceps sinensis* is *Cordyceps sinensis* MF-20008.

* * * * *